US012765895B2

(12) United States Patent
Woodard et al.

(10) Patent No.: US 12,765,895 B2
(45) Date of Patent: Oct. 20, 2026

(54) ALIGNMENT DEVICES FOR USE IN CORRECTION OF BONE DEFORMITIES

(71) Applicant: WRIGHT MEDICAL TECHNOLOGY, INC., Memphis, TN (US)

(72) Inventors: Joseph Ryan Woodard, Memphis, TN (US); Johnny McGee, Halls, TN (US); Peter George Mangone, Arden, NC (US)

(73) Assignee: Wright Medical Technology, Inc., Memphis, TN (US)

( * ) Notice: Subject to any disclaimer, the term of this patent is extended or adjusted under 35 U.S.C. 154(b) by 29 days.

(21) Appl. No.: 19/093,413

(22) Filed: Mar. 28, 2025

(65) Prior Publication Data

US 2025/0221720 A1 Jul. 10, 2025

Related U.S. Application Data

(62) Division of application No. 17/904,799, filed as application No. PCT/US2021/022903 on Mar. 18, 2021, now Pat. No. 12,285,180.

(60) Provisional application No. 63/008,854, filed on Apr. 13, 2020.

(51) Int. Cl.
*A61B 17/17* (2006.01)

(52) U.S. Cl.
CPC ................................ *A61B 17/1775* (2016.11)

(58) Field of Classification Search
CPC ... A61B 17/17; A61B 17/1703; A61B 17/171; A61B 17/1714; A61B 17/1732; A61B 17/1739; A61B 17/1775
See application file for complete search history.

(56) References Cited

U.S. PATENT DOCUMENTS

| | | | | |
|---|---|---|---|---|
| 4,672,957 A * | 6/1987 | Hourahane | A61F 2/0811 | 606/80 |
| 4,722,331 A * | 2/1988 | Fox | A61B 17/1714 | 606/80 |
| 5,163,940 A * | 11/1992 | Bourque | A61B 17/1764 | 606/88 |
| 5,688,284 A * | 11/1997 | Chervitz | A61B 17/1714 | 606/88 |
| 6,342,056 B1 * | 1/2002 | Mac-Thiong | A61B 17/1757 | 606/88 |

(Continued)

FOREIGN PATENT DOCUMENTS

| | | | |
|---|---|---|---|
| EP | 3583905 A1 * | 12/2019 | A61B 90/11 |
| WO | WO-2019246332 A1 * | 12/2019 | A61B 90/11 |
| WO | WO-2020123899 A1 * | 6/2020 | A61B 17/15 |

*Primary Examiner* — Eric S Gibson

(74) *Attorney, Agent, or Firm* — DUANE MORRIS LLP

(57) ABSTRACT

An alignment device includes a first member, a second member, and a guide. The first member has an elongated body and is configured to be at least partially inserted into a canal in a first bone portion. The second member includes a body attachable to the first member and an arm extending from the body. The arm defines a track. The guide is configured to translate along the track defined by the arm. The guide includes an aperture configured to receive an alignment member therethrough. The guide is configured to be positioned at a desired position along the track to allow insertion of the at least one alignment member through the aperture and into the first bone portion at a desired trajectory.

14 Claims, 9 Drawing Sheets

(56) References Cited

U.S. PATENT DOCUMENTS

| | | | | |
|---|---|---|---|---|
| 7,594,917 | B2 * | 9/2009 | Whittaker | A61B 17/1714 606/98 |
| 7,842,042 | B2 * | 11/2010 | Reay-Young | A61F 2/0805 606/96 |
| 8,317,862 | B2 * | 11/2012 | Troger | A61B 17/1764 623/13.11 |
| 8,439,925 | B2 * | 5/2013 | Marino | A61B 17/1757 606/104 |
| 8,685,033 | B2 * | 4/2014 | Johnson | A61B 17/1764 606/88 |
| 8,690,885 | B2 * | 4/2014 | Smith | A61B 17/1714 606/96 |
| 8,986,316 | B1 * | 3/2015 | Jordan | A61B 17/1796 606/96 |
| 9,161,764 | B2 * | 10/2015 | Smith | A61B 17/1764 |
| 9,955,982 | B2 * | 5/2018 | Meridew | A61B 17/1714 |
| 10,213,219 | B2 * | 2/2019 | Garlock | A61B 17/1739 |
| 11,246,610 | B2 * | 2/2022 | Lee | A61B 17/1775 |
| 11,419,684 | B2 * | 8/2022 | Pandya | A61B 17/1764 |
| 11,871,943 | B2 * | 1/2024 | Lee | A61B 17/1775 |
| 12,285,180 | B2 * | 4/2025 | Woodard | A61B 17/1775 |
| 2002/0133165 | A1 * | 9/2002 | Whittaker | A61B 17/1764 606/98 |
| 2003/0216742 | A1 * | 11/2003 | Wetzler | A61B 17/17 606/96 |
| 2008/0103506 | A1 * | 5/2008 | Volpi | A61B 17/1764 606/96 |
| 2010/0121337 | A1 * | 5/2010 | Pandya | A61B 17/1714 606/96 |
| 2012/0109136 | A1 * | 5/2012 | Bourque | A61B 17/1714 606/87 |
| 2015/0032168 | A1 * | 1/2015 | Orsak | A61B 17/68 606/304 |
| 2016/0367270 | A1 * | 12/2016 | Garlock | A61B 17/1739 |
| 2020/0060698 | A1 * | 2/2020 | Woodard | A61B 17/1725 |
| 2021/0113223 | A1 * | 4/2021 | Schaumann | A61B 17/1775 |
| 2021/0298771 | A1 * | 9/2021 | Lee | A61B 17/1775 |
| 2022/0167999 | A1 * | 6/2022 | Lee | A61B 17/1775 |
| 2023/0132273 | A1 * | 4/2023 | Woodard | A61B 17/1775 606/87 |
| 2023/0389944 | A1 * | 12/2023 | Lee | A61B 17/1775 |
| 2025/0221720 | A1 * | 7/2025 | Woodard | A61B 17/1775 |

* cited by examiner

ALIGNMENT DEVICES FOR USE IN CORRECTION OF BONE DEFORMITIES

CROSS-REFERENCE TO RELATED APPLICATIONS

Any and all applications for which a foreign or domestic priority claim is identified in the Application Data Sheet as filed with the present application are hereby incorporated by reference in accordance with 37 C.F.R. §§ 1.57; 1.97; and 1.98.

BACKGROUND

During surgery, such as foot surgery, it may be necessary to fix a position of a first bone fragment and a second bone fragment. For example, in some instances, an osteotomy is formed in a bone to correct one or more defects. After forming the osteotomy, a first fragment of the bone and a second fragment of a bone are positioned to correct the defect and are fixed in place using one or more fixation elements. In other embodiments, one or more bone fragments are formed as a result of an injury and/or medical procedure.

Current systems rely on the placement of guide elements prior to insertion of the fixation elements. Placement of the guide elements is performed by a surgeon and often requires the surgeon to insert and remove the guide element several times before a desired placement is achieved. The repeated insertion and removal of guide elements results in additional wounds in a patient and increased pain, recovery time, and complexity of surgery (including difficulty, increased surgical time, etc.)

SUMMARY

In one aspect, an alignment device includes a first member, a second member, and a guide. The first member has an elongated body configured to be at least partially inserted into a first bone portion. The second member includes a body attachable to the first member and an arm extending from the body. The arm defines a track. The guide includes a body configured to translate along the track defined by the arm. The body defines an aperture configured to receive an alignment member therethrough. The body of the guide is configured to be positioned at a desired position along the track to allow insertion of the at least one alignment member through the aperture and into the first bone portion at a desired trajectory.

In another aspect, an alignment device is provided for guiding insertion of an alignment member into a first portion of a first metatarsal and a second portion of the first metatarsal after separation of the first portion from the second portion. The alignment device includes a first member, a second member, and a guide. The first member has an elongated body configured for at least partial insertion into a canal in the first portion of the first metatarsal and to be used to displace the first portion relative to the second portion. The second member includes a body attachable to the first member and an arm extending from the body. The arm defines a track. The guide includes a body configured to translate along the track defined by the arm. The body defines an aperture configured to receive an alignment member therethrough. The body of the guide is configured to be positioned at a desired position along the track to allow insertion of the alignment member through the aperture and into the first bone portion at a desired trajectory such that the alignment member passes through the first bone portion and into the second bone portion.

In another aspect, a system includes a K-wire and an alignment device. The alignment device includes a first member, a second member, and a guide. The first member has an elongated body configured to be at least partially inserted into a canal in a first bone portion. The second member includes a body attachable to the first member and an arm extending from the body. The arm defines a track. The guide includes a body configured to translate along the track defined by the arm. The body defines an aperture configured to receive the K-wire therethrough. The body of the guide is configured to be positioned at a desired position along the track to allow insertion of the K-wire through the aperture and into the first bone portion at a desired trajectory.

In another aspect, a method includes performing an osteotomy to separate a first bone portion from a second bone portion. The method further includes inserting an elongated body of a first member partially into a canal in the first bone portion. The method further includes positioning a body of a guide at a desired position along a track of an arm of a second member that is attached to the first member. The method further includes locking the body of the guide at the desired position. The method further includes inserting an alignment member through an aperture in the body of the guide and into the first bone portion.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

DETAILED DESCRIPTION

Figure 1:
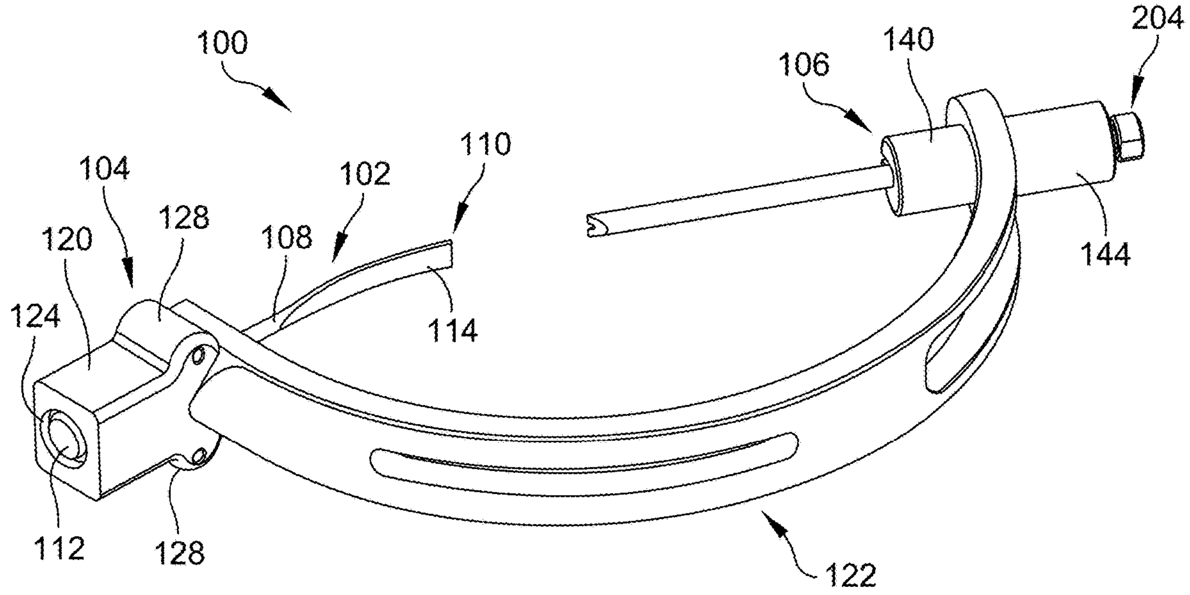
FIGS. 1-3 are perspective views of an alignment device, according to a first embodiment described herein.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as “horizontal,” “vertical,” “up,” “down,” “top,” and “bottom” as well as derivatives thereof (e.g., “horizontally,” “downwardly,” “upwardly,” etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The devices described herein can be used after performing a minimally-invasive distal osteotomy of the first metatarsal. The devices include a first member for use in displacing and positioning the proximal portion of the metatarsal after the osteotomy is performed. The devices further include a second member for positioning a guide that is used for inserting a K-wire into the proximal and distal portions of the first metatarsal to fix temporarily the position of the portions of the metatarsal until the positions of the metatarsal are fixed using screws, plates, or other fixation means. These devices simplify the process of fixing the positions of the portions of the metatarsal and reduce the burden on the surgeon performing the procedure.

Figure 2:
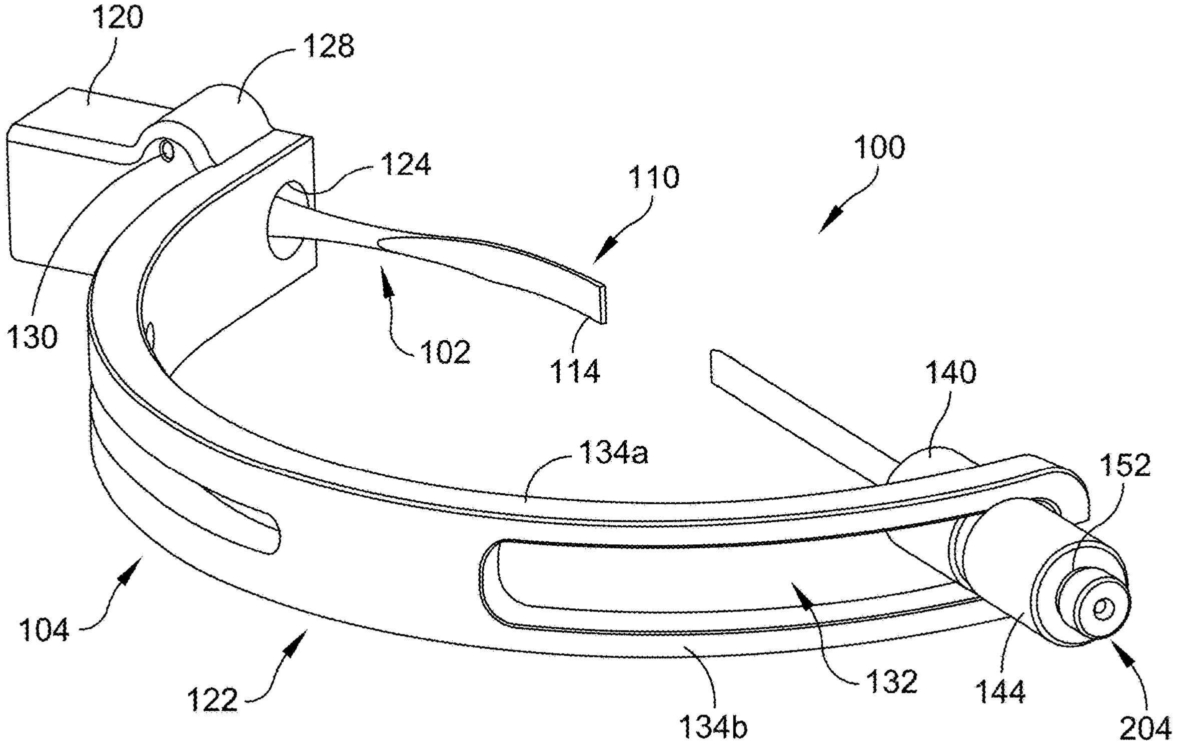
Figure 3:
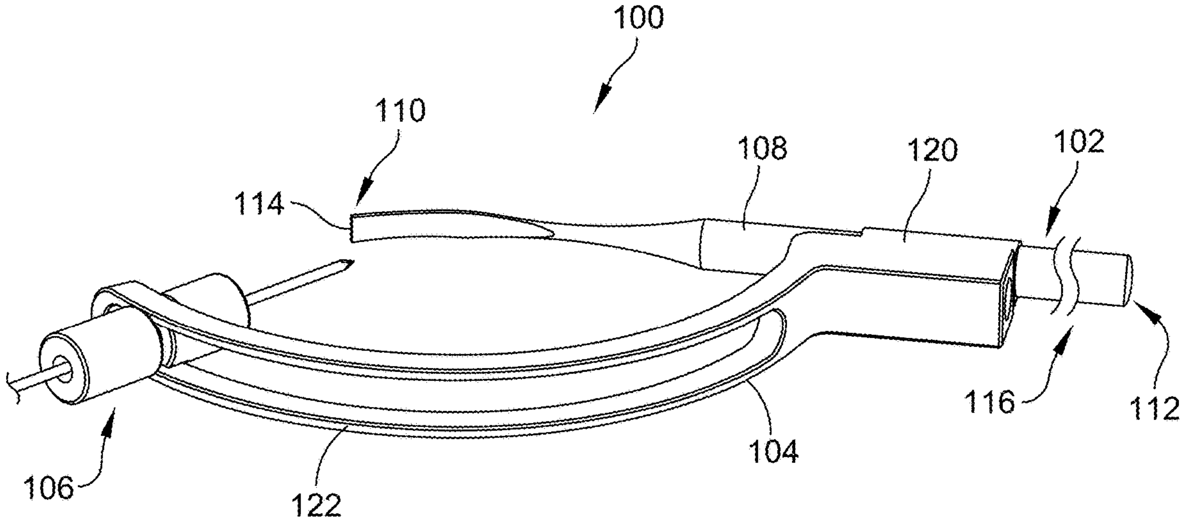

As shown in FIGS. 1-4, in one embodiment, an alignment device 100 includes a first member 102, a second member 104, and a guide 106. The first member 102 has an elongated body 108 that is configured to be at least partially inserted into a canal in a first portion 300 of the metatarsal (e.g., the proximal portion shown in FIG. 9). The elongated body 108 extends from a first end 110 to a second end 112. At the first end 110, the elongated body 108 may be in the form of a thin blade 114. The blade 114 is configured to be inserted into the medullary canal of the first portion 300 of the bone. Further, the blade 114 can follow an arcuate path to allow for easier insertion into the medullary canal. As best seen in FIG. 3, the elongated body 108 further includes a second portion 116 extending from the blade 114 and toward the second end 112. The second portion 116 can be cylindrical and be of a diameter that is comfortable for handling and manipulation by a surgeon. As will be described in more detail below, the second portion 116 of the first member 102 may be held by the surgeon to insert the blade 114 into the first portion 300 of the bone and while displacing the first portion 300 of the bone relative to the second portion 302.

Figure 4:
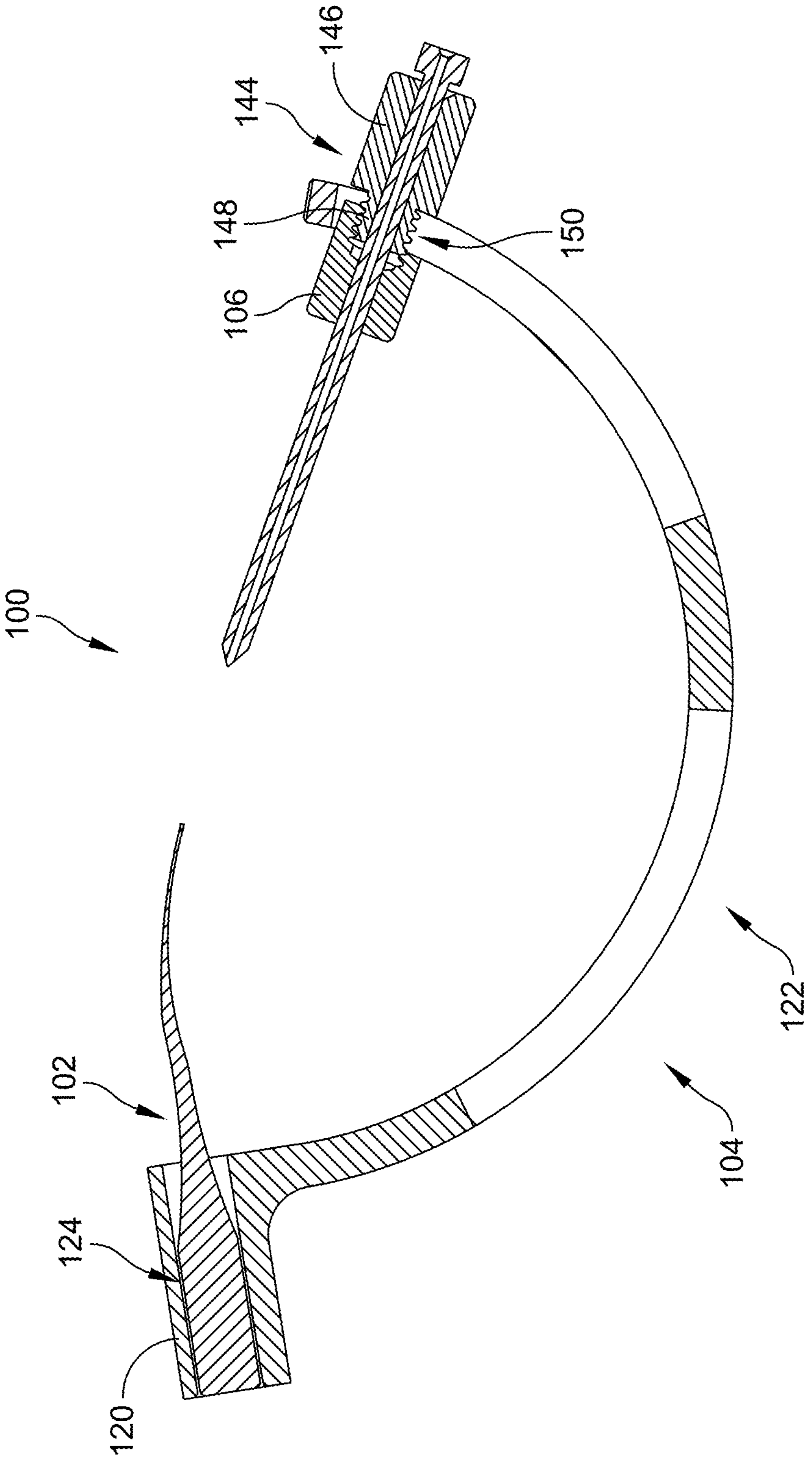
FIG. 4 is a cross-sectional view of the alignment device of FIGS. 1-3.
Figure 5:
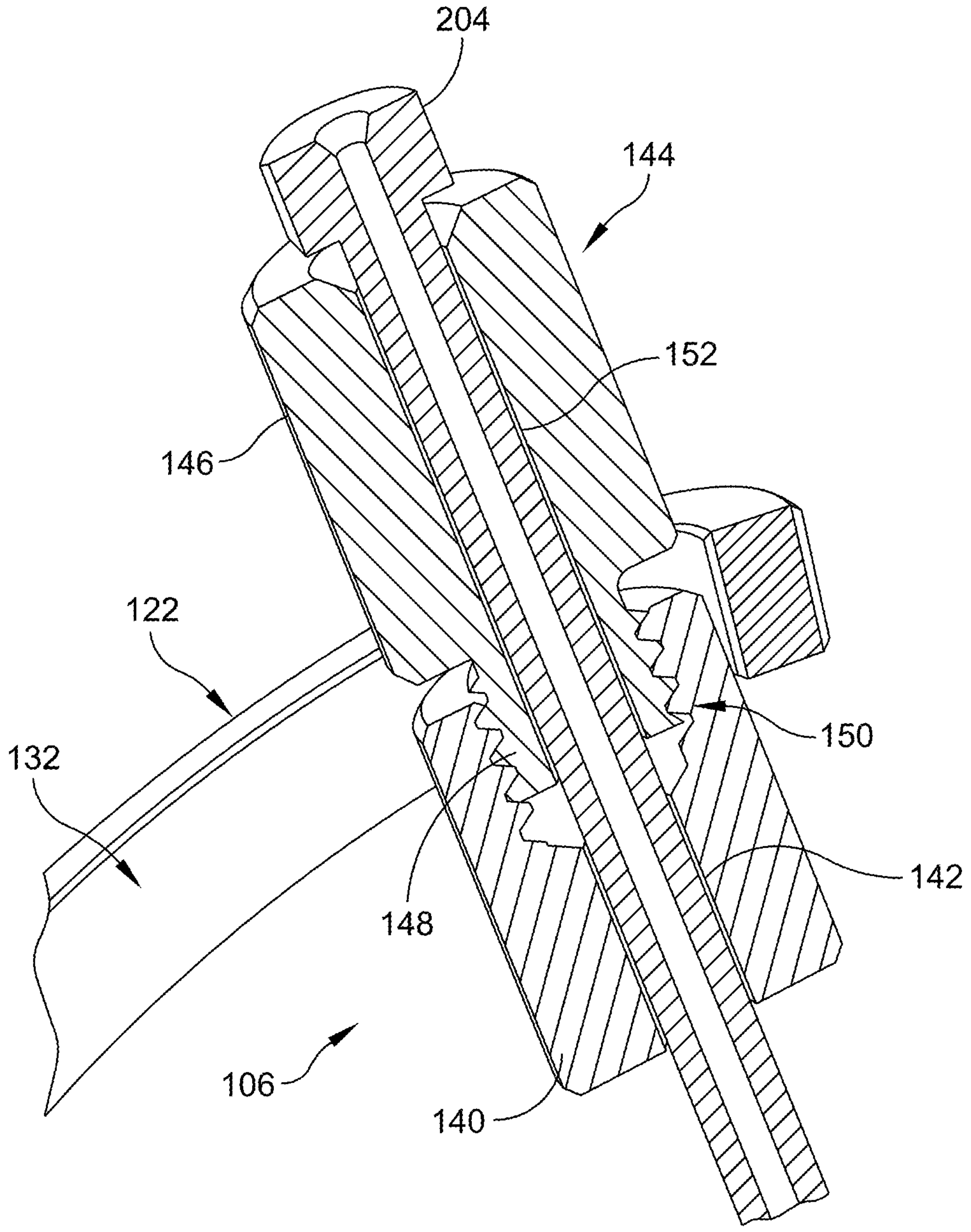
FIG. 5 is a detail cross-sectional view of the guide of the alignment device of FIGS. 1-3.

The second member 104 includes a body 120 and an arm 122. The body 120 is attachable to the first member 102. It should be understood that the body 120 being attachable to the first member encompasses both permanent or fixed attachment as well as removable attachment, as described further herein. In one embodiment, as best shown in FIGS. 4 and 5, the body 120 defines a passage 124 configured to receive the second portion 116 of the elongated body 108 of the first member 102. In such embodiments, the second member 104 can be remove ably attachable to the first member 102. Specifically, the passage 124 in the body 120 of the second member 104 can be passed over the second portion 116 of the elongated body 108 of the first member 102. The passage 124 can be sized and dimensioned to fit closely to the second portion 116 of the elongated body 108 so that, with the second member 104 attached to the first member 102, relative movement of the two is limited. As shown in FIG. 3, the second portion 116 may be sufficiently long to extend through the body 120 to allow for manipulation by the surgeon. In other embodiments, the second member 104 is fixedly attached to the first member 102. For example, the first member 102 may be attached to the body 120 by welding or adhesive or may be held fixedly in place by screws or pins.

As shown in FIG. 1, the second member 104 can include one or more wings 128 extending outward from the body 120. Each of the wings 128 define at least one attachment bore 130 configured to receive an attachment member 200 (shown in FIG. 10) therethrough to secure the second member 104 to the second portion 302 of the metatarsal (i.e., the distal portion of the metatarsal). As described further herein, securing the second member 104 to the second portion 302 prevents rotation of the second member 104 during use to ensure proper positioning alignment of device 100. The alignment bores 130 may be oriented at an angle such that, when the alignment device 100 is secured to the bone, the central axes define an acute angle with respect to the sagittal plane. The attachment member 200 is preferably a K-wire (i.e., a Kirschner wire). However, it should be understood that other elongated wire- or pin-like components can be used—such as, for example, a Steinmann pin.

The arm 122 of the second member 104 extends from the body 120 and defines a track 132. As shown in FIG. 2, the arm 122 can include a first extension **134*a* and a second extension 134*b* spaced apart from, and extending parallel to, the first extension 134*a*. The track 132 is defined between the first 134*a* and second 134*b* extensions. The first 134*a* and second 134*b* extensions can be connected at both ends. The arm 122 follows an arcuate path so that the guide 106 (FIG. 1) can be used to target an alignment member through the first portion 300** of the metatarsal, as described in further detail below.

The guide 106 (FIG. 5) includes a first guide body 140 at least partially disposed in, and configured to translate along, the track 132 defined by the arm 122. The first guide body 140 defines an aperture 142 configured to receive an alignment member, drill, or drill sleeve therethrough. The first guide body 140 of the guide 106 is configured to be positioned at a desired position along the track 132 to allow insertion of the alignment member through the aperture 142 and into the first bone portion 300 at a desired trajectory. The aperture 142 can also be used to guide a drill to form a hole in the first bone portion 300 for receiving the alignment member. The aperture 142 has a central aperture axis A. As described in further detail herein, and shown in FIG. 10, the angle θ defined by the aperture axis A and a longitudinal axis B of the first bone portion 300 changes as the guide 106 is translated along the track 132.

The guide 106 can further include a second guide body 144 having a knob portion 146 and a shaft 148. The shaft 148 of the second guide body 144 engages a hole 150 in the first guide body 140. The shaft 148 can include external threads configured to engage internal threads of the hole 150. As such, the first guide body 140 and the second guide body 144 are engaged such that rotation of the second guide body 144 with respect to the first guide body 140 tightens the guide 106 on the arm 122 to restrict translation of the guide 106 within the track 132. In other embodiments (not shown), the arm 122 includes ratchet teeth and the guide 106 includes an engagement tooth configured to selectively engage one of the ratchet teeth to selectively position the guide 106 along the arm 122.

In some embodiments, as shown in FIGS. 4 and 5, the second guide body 144 includes an aperture 152 aligned with the aperture 142 in the first guide body 140. In such embodiments, the alignment member, drill, or drill sleeve 204 can be inserted through both apertures 142, 152. In other embodiments, as described further herein, the aperture 142 in the first guide body 140 is positioned to the side of the second guide body 144 and the second guide body 144 does not include an aperture.

The guide 106 can include one or more than one guide aperture such that one or multiple alignment members can be inserted into the bone. For example, in the embodiment shown in FIGS. 4 and 5, the apertures 142, 152 extend through the center of the first guide body 140 and the second guide body 144 such that a single alignment member may be inserted into the bone. In such embodiments, when an alignment member is inserted through the aperture 142, 152 it passes through the track 132 of the arm 122.

Figure 6:
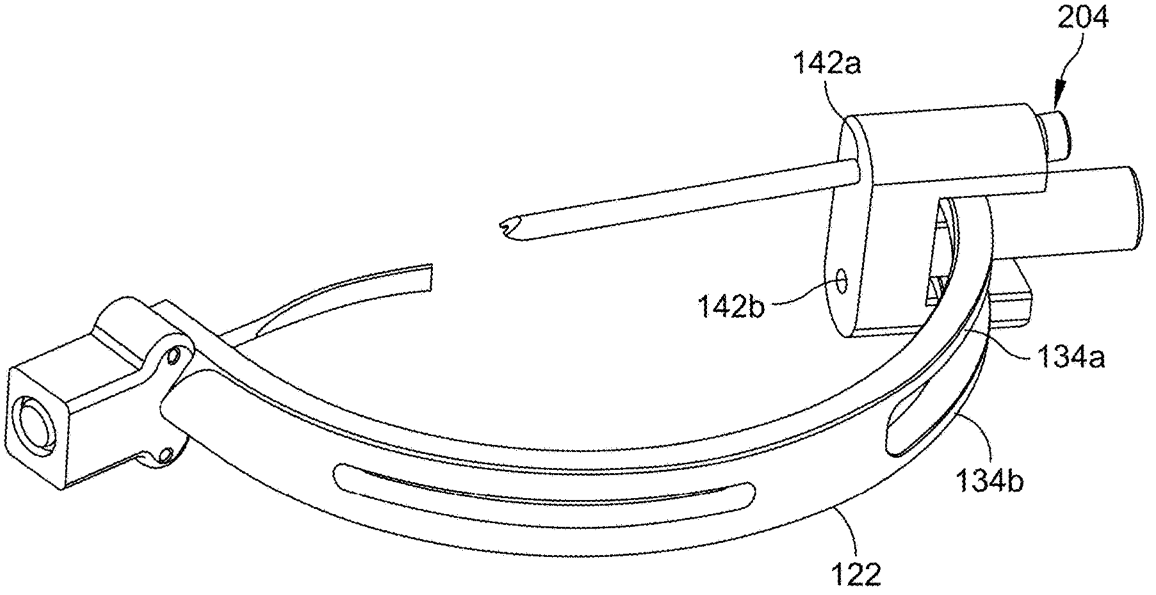
FIG. 6 is a perspective view of an alignment device, according to another embodiment described herein.
Figure 7:
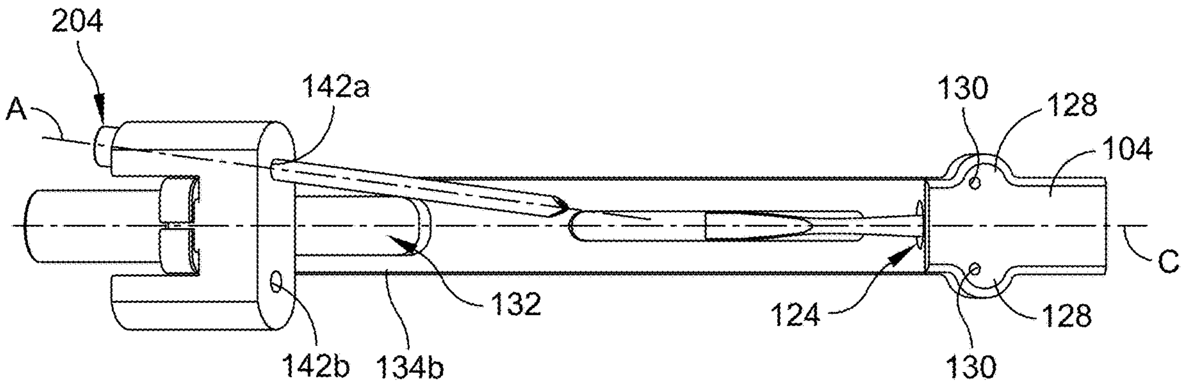
FIG. 7 is a front view of the alignment device of FIG. 6.

In other embodiments, as shown in FIGS. 6 and 7, the guide aperture 142 is positioned such that it is outside the track 132—in other words, offset from the center plane of the alignment device 100. In such embodiments, a single guide aperture 142 can be provided on one side of the arm 122 and the alignment device 100 can be provided in both a left and right version.

Alternatively, the first guide body 140 can define more than one guide aperture 142. For example, in one embodiment, as shown in FIGS. 6 and 7, the first guide body 140 defines two guide apertures 142, one on each side of the arm 122. Specifically, one guide aperture **142*a* is outside of the track 132 and is adjacent to the first extension 134*a* and a second guide aperture 142*b* is outside of the track 132 and is adjacent to the second extension 134*b*. By providing a guide aperture 142 on either side of the track 132, the embodiment shown in FIGS. 6 and 7 can be used on either the left or the right foot; in each case only one of the guide apertures 142 need be used during the procedure. For example, as shown in FIGS. 6 and 7, a drill sleeve 204 can be inserted into the first guide aperture 142*a***.

In embodiments in which the guide aperture 142 is positioned outside of the track 132, the guide aperture 142 may be oriented such that the central aperture axis A is oriented at an acute angle with respect to a central passage axis C of the passage 124 in the body 120 in a vertical plane including the central passage axis C, as shown in FIG. 7. This orientation may guide the drill and the alignment member such that the alignment member passes through the first bone portion 300 and into approximately the center of the cut face of the second bone portion 302.

Figure 8:
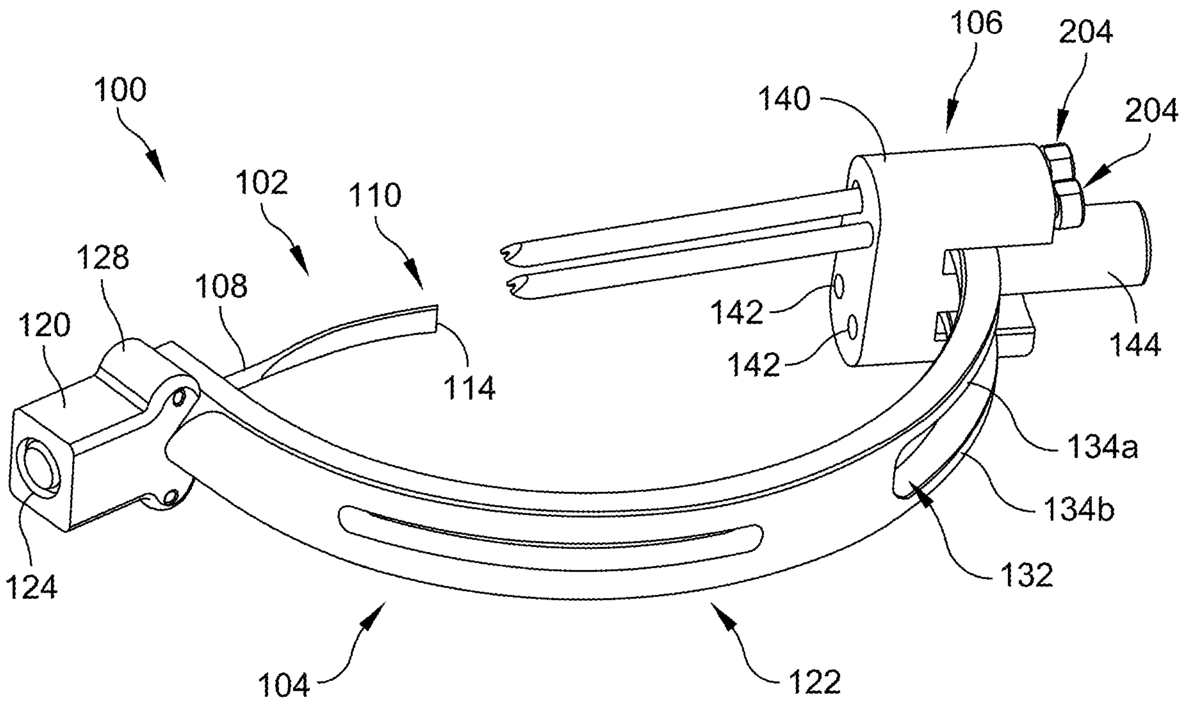
FIG. 8 is a perspective view of an alignment device, according to another embodiment described herein.

In still other embodiments, the first guide body 140 defines more than one guide apertures 142 on each side of the arm 122, as shown in FIG. 8. This may allow the surgeon to insert more than one alignment member into the bone during a procedure. Alternatively, the surgeon can choose from the available guide apertures 142 to insert a single alignment member at a desired position and trajectory based on the patient's anatomy and the surgeon's preferences. In some embodiments, the apertures 142 on each side of the arm 122 are parallel to one another such that alignment members inserted therethrough are parallel.

The alignment members used with the alignment guide 100 are preferably K-wires (i.e., a Kirschner wire). However, it should be understood that other elongated wire- or pin-like components can be used—such as, for example, a Steinmann pin.

Figure 11:
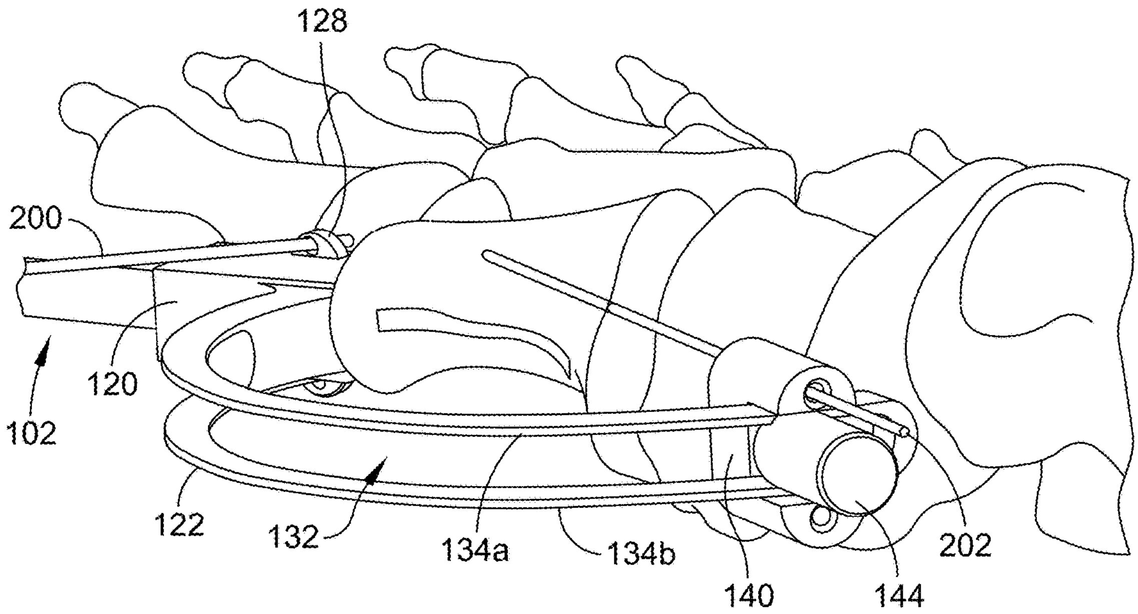
Figure 12:
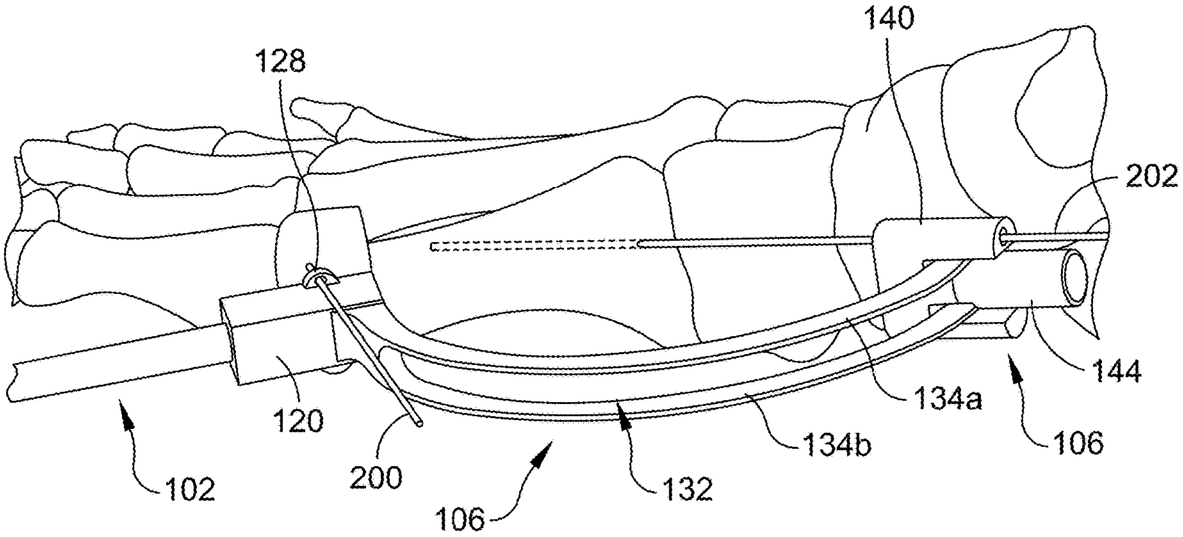
Figure 13:
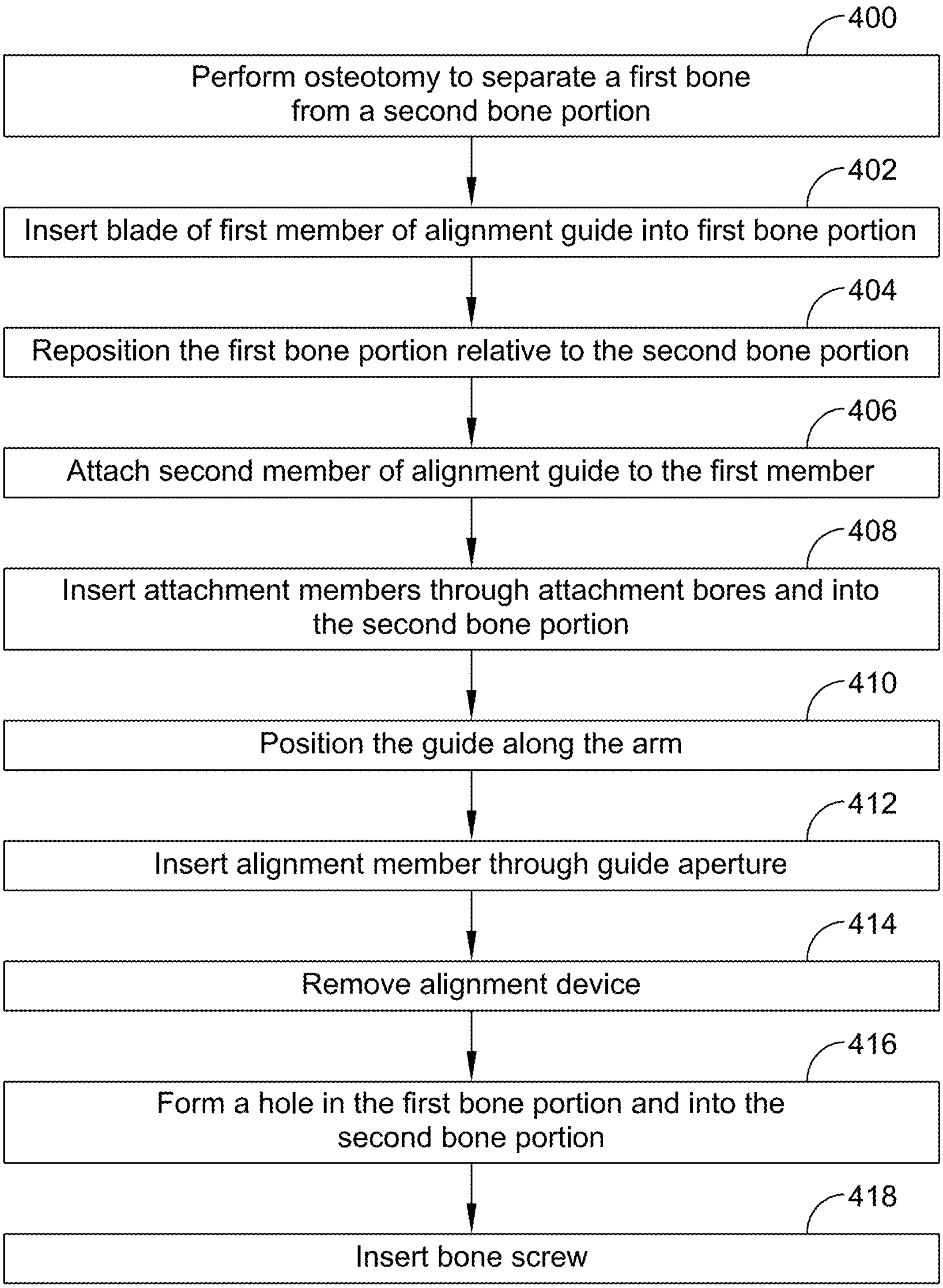
FIG. 13 is a flowchart illustrating a method of correcting a bone deformity using an alignment device as described herein.

FIG. 13 provides a flowchart illustrating a method of correcting a bone deformity and FIGS. 9-12 illustrate various steps of the method. At step 400, an osteotomy is performed to separate a first bone portion 300 from a second bone portion 302. The first bone portion 300 and the second bone portion 302 can be, for example, portions of a first metatarsal. The osteotomy can be a chevron osteotomy, a straight osteotomy, or other suitable osteotomy as will be understood by one of ordinary skill in the art.

At step 402, the blade 114 of the first member 102 is inserted into a canal in the first bone portion 300. The canal can be a medullary canal of the first metatarsal. As described above, the blade 114 can be a flat portion of the first member 102 such that it can be pressed into the soft or spongy bone (i.e., cancellous bone) of the medullary canal. Further, the blade 114 can follow a curved or arcuate path to improve the ergonomics of inserting the blade 114 into the canal.

At step 404, the surgeon uses the first member 102 to reposition the first bone portion 300 relative to the second bone portion 302. Specifically, the surgeon translates the first bone portion 300 medially relative to the second bone portion 302.

Figure 9:
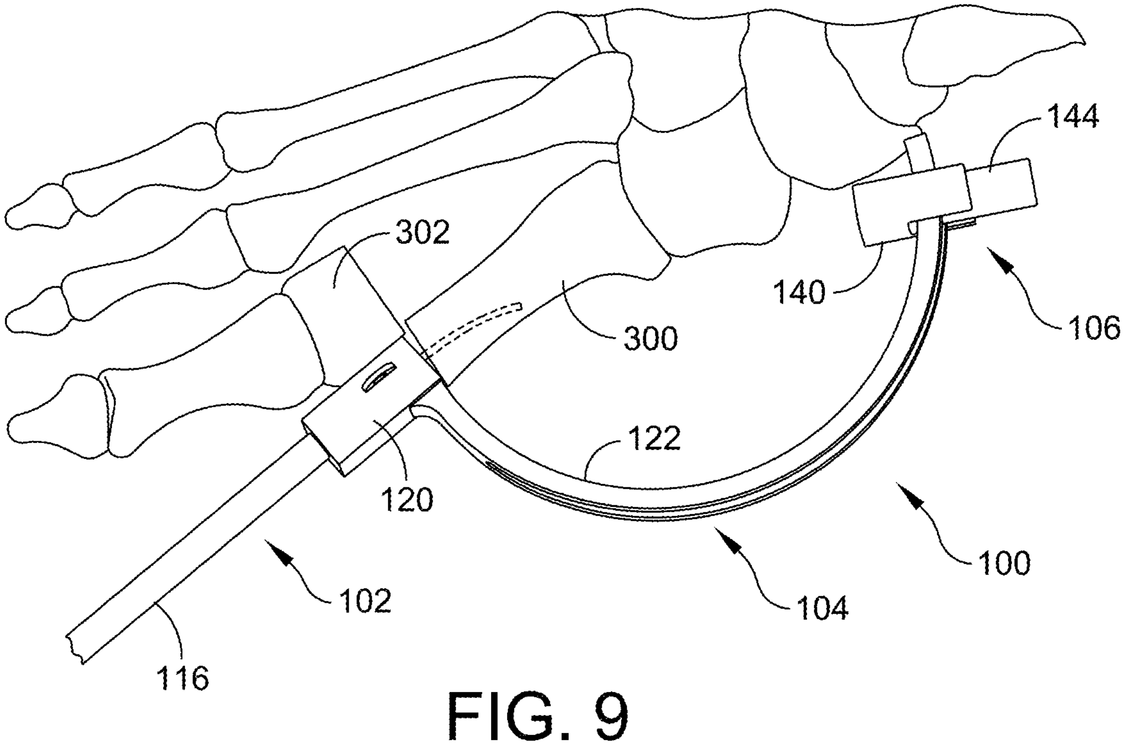
FIGS. 9-12 are views of an alignment device in use.

At step 406, the surgeon attaches the second member 104 to the first member 102. For example, as described above, the surgeon can pass the body 120 of the second member 104 over the first member 102 such that at least a portion of the second portion 116 of the elongated body 108 of the first member 102 extends through the passage 124 defined in the body 120. FIG. 9 shows the second member 104 coupled to the first member 102 after repositioning of the first bone portion 300 relative to the second bone portion 302.

At step 408, an attachment member 200 (shown in FIG. 10) is inserted through an attachment bore 130 defined by the wings 128 of the second member 104 and into the second bone portion 302 to attach the second member 104 to the second bone portion 302. The attachment member 200 limits movement (e.g., rotation) of the second member 104 during the procedure.

At step 410, the guide 106 is positioned along the arm 122 of the second member 104 such that the guide aperture 142 is positioned to guide insertion of an alignment member 202 at a desired trajectory. With the guide 106 in the desired position, the guide 106 is locked in place—for example, by rotating the second guide body 144 relative to the first guide body 140. Fluoroscopy or other imaging modalities can be used to ensure proper alignment of the guide 106.

Figure 10:
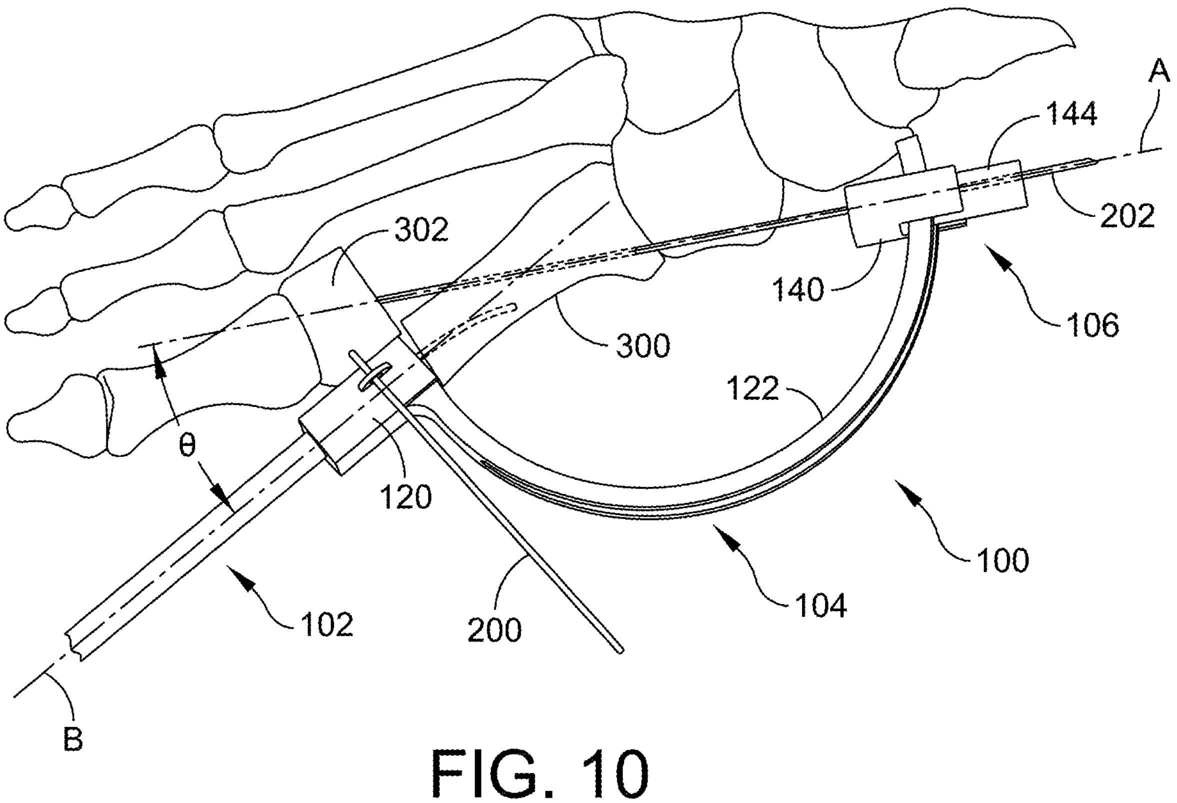

At step 412, at least one alignment member 202 is inserted through a guide aperture 142 in the first guide body 140. The alignment member 202 is inserted through the guide aperture 142, through the first bone portion 300, and into the second bone portion 302. In some embodiments, at step 410, the guide 106 is positioned such that the alignment member 202 is inserted into the second bone portion 302 at approximately the center of the cut face of the second bone portion 302. Optionally, a sleeve 204 can be inserted into the guide aperture 142 to assist with guiding the insertion of the alignment member 202. The sleeve helps guide the alignment member 202 as it is inserted in the first bone portion 300 and prevents skiving of the alignment member 202 (sliding of the tip of the alignment member 202 along the surface of the first bone portion 300) during insertion. FIGS. 10-12 show the alignment device 100 after insertion of the alignment member 202.

At step 414, the alignment device 100 is removed from the alignment member 202 and the first bone portion 300. The second guide body 144 can be rotated until it disengages from the first guide body 140. In embodiments in which the second guide body 144 includes an aperture 152, the second guide body 144 can be slid off the alignment member 202. The attachment member 200 can also be removed from second bone portion 302, thereby allowing for the removal of the first member 102 and the second member 104. Finally, the first guide body 140 can be slid off the alignment member 202.

At step 416, the surgeon can use a cannulated drill bit to form a hole through the first bone portion 300 and into the second bone portion 302 along the trajectory defined by the alignment member 202 by passing the drill bit over the alignment member 202. A drill sleeve 204 can be inserted into the aperture 142 to guide the drill further.

At step 418, a bone screw is inserted into the hole formed in the first bone portion 300 and the second bone portion 302 along the trajectory defined by the alignment member 202 to secure the relative positions of the first bone portion 300 and the second bone portion 302. Additional securement means such as bone plates and staples can also be used to secure the first 300 and second 302 bone portions in position.

In some embodiments, an alignment device includes a first member, a second member, and a guide. The first member has an elongated body configured to be at least partially inserted into a first bone portion. The second member includes a body attachable to the first member and an arm extending from the body. The arm defines a track. The guide has a body configured to be coupled to the arm and translate along the track. The body of the guide defines a first aperture configured to receive an alignment member therethrough. The body of the guide is configured to be positioned at a desired location along the track to allow insertion of the alignment member through the first aperture and into the first bone portion at a desired trajectory.

In some embodiments, the body of the second member defines a passage configured to receive a portion of the elongated body of the first member such that the second member is remove ably attachable to the first member.

In some embodiments, the arm of the second member follows an arcuate path such that, as the guide is translated along the track, an angle defined by a first aperture axis defined by the first aperture and a longitudinal axis defined by the first bone portion changes.

In some embodiments, the body of the second member defines at least one attachment bore, and wherein the attachment bore is configured to receive an attachment member therethrough to secure the second member to a second bone portion.

In some embodiments, the first aperture of the guide is positioned such that, with the alignment member positioned in the first aperture, the alignment member passes through the track.

In some embodiments, the guide defines a second aperture. The first aperture and the second aperture are positioned outside of the track when the guide is coupled to the arm. The first aperture is on the opposite side of the track as the second aperture.

In some embodiments, the alignment member is a K-wire.

In some embodiments, the guide includes a first guide body and a second guide body. The first guide body and the second guide body are engageable such that rotation of the second guide body with respect to the first guide body tightens the guide on the arm to restrict translation of the guide within the track.

In some embodiments, the first aperture passes through the first guide body and the second guide body.

In some embodiments, the body of the second member is permanently attached to the first member.

In some embodiments, an alignment device for guiding insertion of an alignment member into a first portion of a bone and a second portion of the bone after separation of the first portion of the bone from the second portion of the bone is provided. In some embodiments, the alignment device includes a first member, a second member, and a guide. The first member has an elongated body extending from a first end to a second end. The first end is configured to be at least partially inserted into a canal in the first portion of the bone. In some embodiments, the bone is a first metatarsal. The first member is operable to move the first portion of the bone relative to the second portion of the bone. The second member includes a body attachable to the first member and an arm extending from the body. The arm defines a track. The guide is configured to translate along the track defined by the arm. The body of the guide defines a first aperture configured to receive an alignment member therein. The guide is configured to be positioned at a desired location along the track to allow insertion of the alignment member through the aperture and into the first portion of the bone at a desired trajectory such that the alignment member passes through the first portion of the bone and into the second portion of the bone.

In some embodiments, the body of the second member defines a passage configured to receive a portion of the elongated body of the first member such that the second member is remove ably attachable to the first member.

In some embodiments, the arm of the second member follows an arcuate path such that, as the guide is translated along the track, an angle defined by an aperture axis defined by the first aperture and a longitudinal axis defined by the first portion of the bone changes.

In some embodiments, the body of the second member defines at least one attachment bore. The attachment bore is configured to receive an attachment member therethrough to secure the second member to the second portion of the bone.

In some embodiments, the aperture of the guide is positioned such that, with the alignment member positioned in the aperture, the alignment member passes through the track.

In some embodiments, the guide defines a second aperture. The first aperture and the second aperture are positioned outside of the track. The first aperture is located on the opposite side of the track as the second aperture.

In some embodiments, the alignment member is a K-wire.

In some embodiments, the guide includes a first guide body and a second guide body. The first guide body and the second guide body are engageable such that rotation of the second guide body with respect to the first guide body in a first direction tightens the guide on the arm when the guide is received within the track to restrict translation of the guide along the track.

In some embodiments, the first aperture passes through the first guide body and the second guide body.

In some embodiments, the body of the second member is permanently attached to the first member.

In some embodiments, a system or a kit includes an alignment member and an alignment device. The alignment device includes a first member, a second member, and guide. The first member has an elongated body extending from a first end to a second end. The first end sized and configured to be at least partially inserted into a first bone portion. The second member includes a body and an arm extending from the body. The body is sized and configured to receive a portion of the first member. The arm defines a track along a portion of its length. The guide is slideably received within the track defined by the arm of the second member. The body defines a first aperture sized and configured to receive the alignment member therein. The guide is configured to be positioned at a desired location along the track to fix a trajectory of the alignment member release ably relative to the first bone portion.

In some embodiments, the body of the second member defines a passage for receiving the portion of the first member such that the second member is remove ably attachable to the first member.

In some embodiments, the arm of the second member has an arcuate shape, and wherein an angle defined by an aperture axis defined by the aperture and a longitudinal axis of the first bone portion changes as the guide is translated along the track.

In some embodiments, the body of the second member defines at least one attachment bore. The attachment bore is configured to receive an attachment member therethrough to secure the second member to a second bone portion.

In some embodiments, the body of the second member defines a plurality of attachment bores. Each attachment bore of the plurality of attachment bores is configured to receive an attachment member for securing the second member to a portion of bone. In some embodiments, the portion of bone is a second bone portion.

In some embodiments, the first aperture of the guide is positioned such that, with the alignment member positioned in the first aperture, the alignment member passes through the track.

In some embodiments, the guide defines a second aperture. The first aperture and the second aperture are positioned outside of the track. The first aperture is on the opposite side of the track as the second aperture.

In some embodiments, the guide defines a third aperture and a fourth aperture. The third aperture is located adjacent to the first aperture on the opposite side of the track as the second aperture and the fourth aperture.

In some embodiments, the first end of the first member tapers to form a blade.

In some embodiments, the guide includes a first guide body and a second guide body. The first guide body and the second guide body are engageable such that rotation of the second guide body with respect to the first guide body tightens the guide on the arm to fix the guide along a length of the arm within the track.

In some embodiments, the aperture passes through the first guide body and the second guide body.

In some embodiments, a sleeve is insertable through the first aperture defined by the guide. The sleeve is configured to guide insertion of the alignment member.

In some embodiments, a method includes separating a first bone portion from a second portion; inserting at least a portion of a first member into the first bone portion; positioning a body of a guide at a desired position along a track defined by an arm of a second member that is positioned relative to the first member; locking the body of the guide at the desired position; and inserting an alignment member through a first aperture defined by the body of the guide and into the first bone portion.

In some embodiments, inserting the alignment member includes inserting the alignment member through the first bone portion and into the second bone portion.

In some embodiments, positioning the guide includes aligning the first aperture such that when the alignment member is inserted through the first aperture, through the first bone portion, and into the second bone portion. In some embodiments, the alignment member enters the second bone portion at approximately a center of a cut face of the second bone portion.

In some embodiments, the method includes inserting an attachment member through an attachment bore defined by the second member and into the second bone portion to attach the second member to the second bone portion.

In some embodiments, the method includes adjusting a position or orientation of the second bone portion using the second member.

In some embodiments, the method includes removing the guide from the alignment member and removing the first member from the first bone portion; drilling a hole through the first bone portion and into the second bone portion using a cannulated drill guided by the alignment member; and inserting a screw into the hole and into the first bone portion and the second bone portion to fix relative positions of the first bone portion and the second bone portion.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. An alignment device, comprising:

a first member having an elongated body configured to be at least partially inserted into a first bone portion;

a second member comprising:

a body attachable to the first member; and an arm extending from the body, the arm defining a track; and a guide having a body configured to be coupled to the arm and translate along the track, the body of the guide defining a first aperture configured to receive an alignment member therethrough;

wherein the body of the guide is configured to be positioned at a desired location along the track to allow insertion of the alignment member through the first aperture and into the first bone portion at a desired trajectory;

wherein the body of the guide comprises:

a first guide body; and a second guide body;

wherein the first guide body and the second guide body are engageable such that rotation of the second guide body with respect to the first guide body tightens the guide on the arm to restrict translation of the guide within the track; and wherein the first aperture passes through the first guide body and the second guide body.

2. The alignment device of claim 1, wherein the body of the second member defines a passage configured to receive a portion of the elongated body of the first member such that the second member is removably attachable to the first member.

3. The alignment device of claim 1, wherein the arm of the second member follows an arcuate path such that, as the guide is translated along the track, an angle defined by a first aperture axis defined by the first aperture and a longitudinal axis defined by the first bone portion changes.

4. The alignment device of claim 1, wherein the body of the second member defines at least one attachment bore, and wherein the at least one attachment bore is configured to receive an attachment member therethrough to secure the second member to a second bone portion.

5. The alignment device of claim 1, wherein the first aperture of the guide is positioned such that, with the alignment member positioned in the first aperture, the alignment member passes through the track.

6. The alignment device of claim 1, wherein the body of the second member is permanently attached to the first member.

7. An alignment device for guiding insertion of an alignment member into a first portion of a bone and a second portion of the bone after separation of the first portion of the bone from the second portion of the bone, the alignment device comprising:

a first member having an elongated body configured to be at least partially inserted into the first portion of the bone, the first member operable to move the first portion of the bone relative to the second portion of the bone;

a second member comprising:

a body attachable to the first member; and an arm extending from the body, the arm defining a track; and a guide configured to translate along the track defined by the arm, the guide having a body defining a first aperture configured to receive an alignment member therethrough;

wherein the guide is configured to be positioned at a desired location along the track to allow insertion of the alignment member through the first aperture and into the first portion of the bone at a desired trajectory such that the alignment member passes through the first portion of the bone and into the second portion of the bone;

wherein the body of the guide comprises:

a first guide body; and a second guide body;

wherein the first guide body and the second guide body are engageable such that rotation of the second guide body with respect to the first guide body in a first direction tightens the guide on the arm when the guide is received within the track to restrict translation of the guide along the track; and wherein the first aperture passes through the first guide body and the second guide body.

8. The alignment device of claim 7, wherein the body of the second member defines a passage configured to receive a portion of the elongated body of the first member such that the second member is removably attachable to the first member.

9. The alignment device of claim 7, wherein the arm of the second member follows an arcuate path such that, as the guide is translated along the track, an angle defined by an aperture axis defined by the first aperture and a longitudinal axis defined by the first portion of the bone changes.

10. The alignment device of claim 7, wherein the body of the second member defines at least one attachment bore, and wherein the attachment bore is configured to receive an attachment member therethrough to secure the second member to the second portion of the bone.

11. The alignment device of claim 7, wherein the first aperture of the guide is positioned such that, with the alignment member positioned in the first aperture, the alignment member passes through the track.

12. The alignment device of claim 7, wherein the body of the second member is permanently attached to the first member.

13. A system, comprising:

an alignment member; and an alignment device, comprising:

a first member having an elongated body extending from a first end to a second end, the first end sized and configured to be at least partially inserted into a first bone portion;

a second member comprising:

a body sized and configured to receive a portion of the first member; and an arm extending from the body, the arm defining a track along a portion of its length; and a guide slidably received within the track defined by the arm of the second member, the guide having a body defining a first aperture sized and configured to receive the alignment member therein;

wherein the guide is configured to be releasably positioned at a desired location along the track to fix a trajectory of the alignment member relative to the first bone portion;

wherein the body of the guide comprises:

a first guide body; and a second guide body;

wherein the first guide body and the second guide body are engageable such that rotation of the second guide body with respect to the first guide body tightens the guide on the arm to restrict translation of the guide within the track; and wherein the first aperture passes through the first guide body and the second guide body.

14. The system of claim 13, wherein the body of the second member defines a passage for receiving the portion of the first member such that the second member is remove ably attachable to the first member.

* * * * *